US009511006B2

(12) United States Patent
Mundschau et al.

(10) Patent No.: US 9,511,006 B2
(45) Date of Patent: Dec. 6, 2016

(54) DISPERSIBLE MOIST WIPE WITH EMULSION FOR PREVENTION OF SKIN IRRITATION

(71) Applicant: Kimberly-Clark Worldwide, Inc., Neenah, WI (US)

(72) Inventors: Stacy Averic Mundschau, Weyauwega, WI (US); Philip Eugene Kieffer, Winneconne, WI (US); Corey Thomas Cunningham, Larsen, WI (US); Robert E Kasper, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/923,912

(22) Filed: Jun. 21, 2013

(65) Prior Publication Data

US 2014/0004163 A1    Jan. 2, 2014

Related U.S. Application Data

(60) Provisional application No. 61/666,463, filed on Jun. 29, 2012.

(51) Int. Cl.
| | |
|---|---|
| *A61K 8/02* | (2006.01) |
| *A61K 8/891* | (2006.01) |
| *A61Q 19/10* | (2006.01) |
| *A61Q 19/00* | (2006.01) |
| *A61K 8/55* | (2006.01) |
| *A61K 8/73* | (2006.01) |
| *A61K 8/86* | (2006.01) |
| *A61K 8/06* | (2006.01) |

(52) U.S. Cl.
CPC .............. *A61K 8/0208* (2013.01); *A61K 8/062* (2013.01); *A61K 8/55* (2013.01); *A61K 8/73* (2013.01); *A61K 8/733* (2013.01); *A61K 8/86* (2013.01); *A61K 8/891* (2013.01); *A61Q 19/00* (2013.01); *A61Q 19/10* (2013.01); *A61K 2800/75* (2013.01)

(58) Field of Classification Search
None
See application file for complete search history.

(56) References Cited

U.S. PATENT DOCUMENTS

| | | | |
|---|---|---|---|
| 3,896,807 A | 7/1975 | Buchalter | |
| 4,382,919 A | 5/1983 | Alonso et al. | |
| 4,690,821 A | 9/1987 | Smith et al. | |
| 4,772,501 A | 9/1988 | Johnson et al. | |
| 4,806,572 A | 2/1989 | Kellett | |
| 4,904,524 A | 2/1990 | Yoh | |
| 5,110,593 A | 5/1992 | Benford | |
| 5,362,488 A | 11/1994 | Sibley et al. | |
| 5,385,748 A | 1/1995 | Bunger et al. | |
| 5,436,007 A | 7/1995 | Hartung et al. | |
| 5,525,346 A | 6/1996 | Hartung et al. | |
| 5,585,104 A | 12/1996 | Ha et al. | |
| 5,643,588 A | 7/1997 | Roe et al. | |
| 5,648,083 A | 7/1997 | Blieszner et al. | |
| 5,858,335 A | 1/1999 | Lucas et al. | |
| 5,861,145 A | 1/1999 | Lucas et al. | |
| 5,861,147 A | 1/1999 | Dodd et al. | |
| 5,863,663 A | 1/1999 | Mackey et al. | |
| 5,874,067 A | 2/1999 | Lucas et al. | |
| 5,968,025 A | 10/1999 | Roe et al. | |
| 5,985,177 A | 11/1999 | Yoshida et al. | |
| 6,083,854 A | 7/2000 | Bogdanski et al. | |
| 6,103,245 A | 8/2000 | Clark et al. | |
| 6,153,208 A | 11/2000 | McAtee et al. | |
| 6,280,757 B1 | 8/2001 | McAtee et al. | |
| 6,287,581 B1 | 9/2001 | Krzysik et al. | |
| 6,303,119 B1 | 10/2001 | Weisgerber et al. | |
| 6,352,700 B1 | 3/2002 | Luu et al. | |
| 6,410,039 B1 | 6/2002 | Walker | |
| 6,416,788 B1 | 7/2002 | Barr | |
| 6,419,963 B1 | 7/2002 | Niazi | |
| 6,436,418 B1 | 8/2002 | Sheldon et al. | |
| 6,440,437 B1 | 8/2002 | Krzysik et al. | |
| 6,461,601 B1 | 10/2002 | Stoddart et al. | |
| 6,488,943 B1 | 12/2002 | Beerse et al. | |
| 6,500,443 B1 | 12/2002 | Otts et al. | |
| 6,503,524 B1 | 1/2003 | Tyrrell et al. | |
| 6,544,573 B1 | 4/2003 | Pajela et al. | |
| 6,603,053 B2 | 8/2003 | Hisanaka | |
| 6,638,527 B2 | 10/2003 | Gott et al. | |
| 6,696,070 B2 | 2/2004 | Dunn | |
| 6,803,496 B2 | 10/2004 | Elder et al. | |
| 6,831,107 B2 | 12/2004 | Dederen et al. | |
| 6,894,028 B2 | 5/2005 | Lipton et al. | |
| 7,122,238 B2 | 10/2006 | Macedo | |

(Continued)

FOREIGN PATENT DOCUMENTS

| | | |
|---|---|---|
| EP | 0 117 613 B1 | 6/1990 |
| EP | 0 564 307 A1 | 10/1993 |

(Continued)

OTHER PUBLICATIONS

Kamath, M.G. et al., "Spunlace (Hydroentanglement)," Internet web page "http://www.engr.utk.edu/mse/Textiles/Spunlace.htm", Apr. 2004, pp. 1-19.

(Continued)

*Primary Examiner* — Frederick Krass
*Assistant Examiner* — Celeste A Roney
(74) *Attorney, Agent, or Firm* — Kimberly-Clark Worldwide, Inc.

(57) ABSTRACT

A dispersible moist wipe used to clean urine and fecal matter from the skin. The wetting solution is an oil-in-water emulsion containing silicone oil. Phase separation is prevented with one or more gums, propylene glycol alginate, and a Gemini surfactant or phosphate ester.

13 Claims, No Drawings

(56) References Cited

U.S. PATENT DOCUMENTS

| | | |
|---|---|---|
| 7,147,751 B2 | 12/2006 | Shannon et al. |
| 7,169,400 B2 | 1/2007 | Luu et al. |
| 7,195,771 B1 | 3/2007 | Hsu et al. |
| 7,358,279 B2 | 4/2008 | Goget et al. |
| 7,365,030 B2 | 4/2008 | Chamba et al. |
| 7,416,735 B2 | 8/2008 | El-Nokaly et al. |
| 7,592,019 B2 | 9/2009 | Drucks et al. |
| 7,651,691 B2 | 1/2010 | Roso et al. |
| 7,838,477 B2 | 11/2010 | Wenzel et al. |
| 7,951,840 B2 | 5/2011 | Modak et al. |
| 2002/0025334 A1 | 2/2002 | Smith |
| 2002/0120242 A1 | 8/2002 | Tyrrell et al. |
| 2002/0165508 A1 | 11/2002 | Klofta et al. |
| 2003/0035785 A1 | 2/2003 | Palumbo et al. |
| 2003/0045645 A1 | 3/2003 | Chang et al. |
| 2003/0082223 A1 | 5/2003 | Healy et al. |
| 2003/0124373 A1 | 7/2003 | Weuthen et al. |
| 2003/0165449 A1 | 9/2003 | Kaczvinsky et al. |
| 2003/0220042 A1 | 11/2003 | Lostocco et al. |
| 2004/0052834 A1 | 3/2004 | West et al. |
| 2004/0058073 A1 | 3/2004 | Bunyard et al. |
| 2004/0122389 A1 | 6/2004 | Mace et al. |
| 2004/0166183 A1 | 8/2004 | Ruseler-Van Embden et al. |
| 2004/0242097 A1 | 12/2004 | Hasenoehrl et al. |
| 2005/0002994 A1 | 1/2005 | Goppel et al. |
| 2005/0008680 A1* | 1/2005 | Deckner et al. ............... 424/443 |
| 2005/0008681 A1 | 1/2005 | Deckner et al. |
| 2005/0013790 A1* | 1/2005 | Yamaki et al. ................. 424/74 |
| 2005/0031653 A1 | 2/2005 | Kwetkat et al. |
| 2005/0031847 A1 | 2/2005 | Martens et al. |
| 2005/0036960 A1 | 2/2005 | Bussey et al. |
| 2005/0048105 A1 | 3/2005 | McNulty et al. |
| 2005/0058672 A1 | 3/2005 | Gupta |
| 2005/0158369 A1 | 7/2005 | Dorschner et al. |
| 2006/0159645 A1 | 7/2006 | Miller et al. |
| 2006/0171971 A1 | 8/2006 | Marsh et al. |
| 2006/0193819 A1* | 8/2006 | Lu et al. ........................ 424/74 |
| 2006/0210612 A1 | 9/2006 | Simon et al. |
| 2007/0020342 A1 | 1/2007 | Modak et al. |
| 2007/0141127 A1 | 6/2007 | Casas-Sanchez et al. |
| 2007/0254543 A1 | 11/2007 | Bunyard et al. |
| 2008/0145664 A1* | 6/2008 | Sirovatka et al. ......... 428/411.1 |
| 2008/0146484 A1 | 6/2008 | Sirovatka et al. |
| 2008/0207767 A1* | 8/2008 | Dobos et al. .................. 514/724 |
| 2008/0299065 A1* | 12/2008 | Arditty .................... A61K 8/46 424/70.7 |
| 2009/0035229 A1 | 2/2009 | Eirew |
| 2009/0035340 A1 | 2/2009 | Landa et al. |
| 2009/0081269 A1 | 3/2009 | Erazo-Majewicz et al. |
| 2009/0181070 A1 | 7/2009 | Blease et al. |
| 2009/0226498 A1 | 9/2009 | Flugge-Berendes et al. |
| 2009/0263439 A1 | 10/2009 | Casas-Sanchez et al. |
| 2010/0158964 A1 | 6/2010 | Cunningham et al. |
| 2011/0033413 A1 | 2/2011 | Kwetkat et al. |
| 2011/0224637 A1 | 9/2011 | Edgett et al. |
| 2011/0268777 A1 | 11/2011 | Marsh et al. |
| 2011/0318434 A1* | 12/2011 | Guthery ....................... 424/729 |

FOREIGN PATENT DOCUMENTS

| | | |
|---|---|---|
| EP | 0 922 452 A1 | 6/1999 |
| EP | 0 922 456 A1 | 6/1999 |
| EP | 1 192 955 A2 | 4/2002 |
| EP | 1 014 938 B1 | 7/2002 |
| EP | 1 618 925 A1 | 1/2006 |
| EP | 1 992 367 A1 | 11/2008 |
| JP | 01-079108 A | 3/1989 |
| JP | 01-265019 A | 10/1989 |
| WO | WO 97/38735 A1 | 10/1997 |
| WO | WO 99/24551 A1 | 5/1999 |
| WO | WO 99/42131 A1 | 8/1999 |
| WO | WO 99/55303 A1 | 11/1999 |
| WO | WO 01/28339 A2 | 4/2001 |
| WO | WO 01/62224 A1 | 8/2001 |
| WO | WO 02/060502 A2 | 8/2002 |
| WO | WO 2005/044220 A1 | 5/2005 |
| WO | WO 2006/081071 A1 | 8/2006 |
| WO | WO 2007/144814 A1 | 12/2007 |
| WO | WO 2008/129494 A1 | 10/2008 |
| WO | WO 2009/125405 A2 | 10/2009 |

OTHER PUBLICATIONS

Runhe Sea Melody Wet Wipes, sold on Mintel web page "http://www.gnpd.com", Jun. 2010, 2 pages.

* cited by examiner

DISPERSIBLE MOIST WIPE WITH EMULSION FOR PREVENTION OF SKIN IRRITATION

This application claims priority to Provisional Patent Application No. 61/666,463, filed on Jun. 29, 2012. The entirety of Provisional Patent Application No. 61/666,463 is incorporated herein by reference.

BACKGROUND OF THE DISCLOSURE

Dispersible flushable moist products need to exhibit satisfactory in-use strength, but quickly break down in sewer or septic systems. Current dispersible moist wipes do this by using a triggerable, salt-sensitive binder on a substrate made from cellulose-based fibers. The binder attaches to cellulose fibers to form a network having adequate in-use strength in a salt solution, but swells and disintegrates in the fresh water of a toilet and sewer system. Electrolytes such as sodium chloride and sodium benzoate are used to keep a moist wipe intact until diluted with water.

There is a great desire to provide higher order skin benefits and aesthetic properties to dispersible moist wipes. One way to do this is by wetting the wipe substrate with a wetting composition such as an emulsion that includes therapeutic amounts of silicone oil as a skin barrier. Emulsions are preferred over solutions because they can impart oils to the skin for the prevention of diaper dermatitis (diaper rash) and provide benefits such as emolliency, moisturization whereas solutions cannot. However, while emulsions present benefits, problems arise when using them as dispersible, moist-wipe wetting compositions. The biggest problem to overcome is the phase separation that occurs when combining electrolytes and oils at therapeutic concentrations in an emulsion.

While there are several methods to achieve stable emulsions having a combination of electrolytes and oils at the specified concentrations, there are several disadvantages associated with these methods. First, the concentration of emulsifier required to successfully stabilize an emulsion containing a silicone oil, such as dimethicone can be so great that it is cost prohibitive. Second, obtaining a low-viscosity, sprayable solution can be difficult due to the high probability that oil droplets will coalesce, particularly at the elevated temperatures to which the solution may be exposed. Third, without appropriately modifying the rheology of the water phase, emulsions with a low viscosity and low solids content tend to undergo phase separation, particularly following a freeze-thaw cycle. This results in a product that would not be efficacious because some areas of the wipe would have higher concentrations of the oil and other areas with less or even no oil present.

There remains a need for a cost-effective, dispersible moist wipe with an emulsion-based wetting composition that does not phase separate with the addition of an electrolyte, even after a freeze-thaw cycle. It would be further advantageous if such wetting composition had a viscosity suitable for spraying onto a wipe substrate.

BRIEF DESCRIPTION OF THE DISCLOSURE

It has been unexpectedly found that a dispersible moist-wipe wetting composition containing therapeutic amounts of oil and electrolytes can be made stable with the addition of an emulsifier system and a stability enhancing system. In particular, the stability enhancing system contains one or more types of gum and propylene glycol alginate. One or more of the following gum(s) may be suitable: xanthan gum, guar gum, gellan gum, acacia gum, cellulose gum, dehydroxanthan gum, sclerotium gum and locust bean gum. Further, the gums are also salt tolerant as compared to typical rheology modifiers like acrylates, carbomer, polyquaternium-37, etc.

Without being bound by theory, it is believed that propylene glycol alginate in combination with one or more gums provides an improved freeze-thaw stability by not only increasing the density of the water phase, but by imparting additional emulsification.

Accordingly, in one aspect, the present disclosure is directed to a dispersible moist wipe with a wetting composition in the form of an oil-in-water emulsion. The wetting composition includes a salt-tolerant emulsifier; a gum blend; 1% to 10% by weight silicone oil; 85% to 98% by weight water and a salt in an effective amount to preserve the wet strength of the wipe substrate during storage. The gum blend includes a gum and propylene glycol alginate, wherein the gum blend is less than or equal to 0.5% weight of the emulsion.

In one aspect of the disclosure is a moist wipe having a wetting composition for the prevention of skin irritation, the wetting composition including: a Gemini surfactant or phosphate ester; a gum blend made with at least one gum and propylene glycol alginate, wherein the amount of the gum blend is 0.01% to 0.5% by weight; 1% to 10% by weight silicone oil; 85% to 98% by weight water; a salt containing monovalent and/or divalent ions; and a dispersible substrate onto which the wetting composition has been applied; wherein the amount of salt is that which is effective to preserve the wet strength of the dispersible substrate during storage.

In another aspect of the disclosure is a moist wipe having above noted wetting composition for the prevention of skin irritation applied to a substrate.

In yet another aspect of the invention is a wetting composition for a moist wipe including a Gemini surfactant or phosphate ester; a gum blend including xanthan gum, guar gum and propylene glycol alginate, wherein the amount of gum blend is 0.05% to 0.5% by weight; 1% to 10% by weight silicone oil; 1% to 3% salt containing monovalent and/or divalent ions; and 85% to 98% by weight water.

Advantages due to the wetting composition of the present disclosure include but are not limited to the following: cost effectiveness due to lower concentrations of emulsifier, the capability of being applied to a wipe substrate by spraying, and physical stability despite a combination of electrolytes and therapeutic amounts of oils of interest. Another aspect of the invention is the use of silicone oils which are difficult to emulsify, particularly in the presence of high levels of electrolytes.

DETAILED DESCRIPTION OF THE DISCLOSURE

The present disclosure is directed to a dispersible moist wipe wetted with a composition for the prevention of skin irritation or imparting other benefits such as moisturization or improved aesthetics. The wetting composition is an oil-in-water, salt tolerant emulsion that includes among other ingredients, an emulsifier system and a stability enhancing system of a gum blend and propylene glycol alginate. Surprisingly, the wetting composition of the present disclosure maintains physical stability even when subjected to three or more freeze-thaw cycles.

Generally, the dispersible moist wipe of the present disclosure is a water-dispersible substrate held together with an ion-sensitive binding polymer and wetted with an oil-in-water wetting composition. The wetting composition is formulated with a carrier medium, a silicone oil, an emulsifier system, a stability enhancing system and an insolubilizing agent (in this case, an electrolyte). Additional ingredients, e.g. fragrance, botanicals, pH adjusting agents, buffers, preservatives, moisturizers and the like may be added to the wetting composition.

Wipe Substrate

In many personal care products, nonwoven materials are the preferred substrate, especially with regard to moist wipes. Nonwoven materials may comprise either nonwoven fabrics or nonwoven webs. Nonwoven fabrics may be made from a variety of processes including, but not limited to, airlaid processes, wet-laid processes such as with cellulosic-based tissues or towels, hydroentangling processes, staple fiber carding and bonding, and solution spinning. Nonwoven webs are fibrous materials having a structure of individual fibers or filaments randomly arranged into a mat-like substrate. Where nonwoven fabrics are simply made with fibrous material, and nonwoven webs are typically made with fibrous material and a binder composition.

Because the moist wipes of the present invention are meant to be dispersible, the appropriate choice for a substrate is a nonwoven web. Desirably, the fibrous material used to form the nonwoven web of the present disclosure has a low wet cohesive-strength prior to its treatment with a binder composition so that when the binder composition is diluted with water, the nonwoven web disperses and is appropriate for flushing into a sewer or septic system.

The fibers of the fibrous material may be made from a variety of materials including natural fibers, synthetic fibers, and combinations thereof. The choice of fibers may depend upon, for example, the intended end use of the finished substrate, as well as the fiber cost. For instance, suitable fibers may include, but are not limited to, natural fibers such as cotton, linen, jute, hemp, wool, wood pulp, etc. Similarly, suitable fibers may also include, but are not limited to, regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as lyocell.

Among wood pulp fibers, any known papermaking fibers may be used, including softwood and hardwood fibers. These fibers may be chemically or mechanically pulped, bleached or unbleached, virgin or recycled, high or low yield, and the like. Chemically treated natural cellulosic fibers can be used, such as mercerized pulps, chemically stiffened or crosslinked fibers or sulfonated fibers. In addition, cellulose produced by microbes and other cellulosic derivatives can be used.

As used herein "cellulosic" is defined as any material having cellulose as a major constituent, and specifically, having at least 50 percent by weight cellulose or cellulose derivative. Thus, the term cellulosic encompasses cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose (biopulp). Blends of one or more of any of the previously described fibers may be used as desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber. In those instances where the fibrous material includes multiple layers, the binder composition of the present disclosure may be applied to the entire thickness of the fibrous material, or each individual layer may be separately treated and then combined with other layers in a juxtaposed relationship to form the finished fibrous material.

Airlaid nonwoven fabrics are particularly well suited for use as moist wipes. The basis weights for airlaid nonwoven fabrics may range from about 20 to about 200 grams per square meter (gsm) with staple fibers having a denier of about 0.5-10 and a length of about 6-15 millimeters. Moist wipes may generally have a fiber density of about 0.025 g/cc to about 0.2 g/cc. Moist wipes may generally have a basis weight of about 20 gsm to about 150 gsm, such as between about 30 to about 90 gsm or about 50 gsm to about 60 gsm.

Binder Composition

The binder composition of the present disclosure includes a triggerable polymer and an optional cobinder. A variety of triggerable polymers may be used, one such type being a dilution triggerable polymer. Examples of dilution triggerable polymers include ion-sensitive polymers, which may be used in combination with a wetting composition in which the insolubilizing agent is a salt.

If the dilution triggerable polymer is an ion-sensitive polymer derived from one or more monomers, where at least one monomer contains an anionic functionality, the ion-sensitive polymer is referred to as an "anionic ion-sensitive polymer". If the ion-sensitive polymer is derived from one or more monomers, where at least one monomer contains a cationic functionality, the ion-sensitive polymer is referred to as a "cationic ion-sensitive polymer".

An exemplary anionic ion-sensitive polymer is described in U.S. Pat. No. 6,423,804, which is incorporated herein in its entirety by reference except that in the event of any inconsistent disclosure or definition from the present application, the disclosure or definition herein shall be deemed to prevail.

Examples of cationic ion-sensitive polymers are disclosed in the following U.S. Patent Publication Nos.: 2004/0058600, 2003/0027270, 2003/0032352, and 2004/0030080; and U.S. Pat. Nos. 6,828,014; 6,897,168; 6,908,966; 6,960,371; 6,994,865; 7,070,854; 7,101,456; 7,141,519 and 7,157,389, all of which are incorporated herein by reference in their entirety, except that in the event of any inconsistent disclosure or definition from the present application, the disclosure or definition herein shall be deemed to prevail.

The ion-sensitive polymer is insoluble in the wetting composition that contains at least about 0.3 weight percent of an insolubilizing agent. The insolubilizing agent may include one or more inorganic and/or organic salts containing monovalent and/or divalent ions. More desirably, the ion-sensitive polymer may be insoluble in the wetting composition, wherein the wetting composition includes from about 0.3 to about 3.5 percent by weight of an insolubilizing agent, which may in turn include one or more inorganic and/or organic salts containing monovalent and/or divalent ions. Even more desirably, the ion-sensitive polymer may be insoluble in the wetting composition, wherein the wetting composition includes from about 0.5 to about 3.5 percent by weight of an insolubilizing agent, which in turn includes one or more inorganic and/or organic salts containing monovalent and/or divalent ions. Most desirably, the ion-sensitive polymer may be insoluble in the wetting composition, wherein the wetting composition includes from about 1 to about 3 percent by weight of an insolubilizing agent, which in turn includes one or more inorganic and/or organic salts containing monovalent and/or divalent ions. Suitable monovalent ions include, but are not limited to, $Na^+$ ions, $K^+$ ions, $Li^+$ ions, $NH_4^+$ ions, low molecular weight quaternary ammonium compounds (e.g., those having fewer than five carbons on any side group), and a combination thereof. Suitable divalent ions include, but are not limited to, $Zn^{2+}$, $Ca^{2+}$ and $Mg^{2+}$. These monovalent and divalent ions may be derived from organic and inorganic salts including, but not limited to, NaCl, NaBr, KCl, $NH_4Cl$, $Na_2SO_4$, Sodium Citrate, Sodium Benzoate, $ZnCl_2$, $CaCl_2$, $MgSO_4$, and combinations thereof. Typically, alkali metal halides are the most desirable monovalent or divalent ions because of cost, purity, low toxicity and availability. A most desirable salt is NaCl (sodium chloride).

In one aspect of the disclosure, the ion-sensitive polymer provides the nonwoven web with sufficient in-use strength (typically >300 gf/in) in combination with the wetting composition containing sodium chloride. These nonwoven webs may be dispersible in tap water, and desirably lose most of their wet strength (<100 gf/in) in 24 hours or less.

In another aspect of the present disclosure, the ion-sensitive polymer includes a cationic sensitive polymer, which is a cationic polyacrylate that may be the polymerization product of 96 mol percent methyl acrylate and 4 mol percent [2-(acryloyloxy)ethyl]trimethyl ammonium chloride.

As previously discussed, the binder composition may comprise a triggerable polymer and optional cobinder. When the binder composition comprises both a triggerable polymer and a cobinder, desirably, the triggerable polymer and cobinder are compatible with each other in aqueous solutions to: 1) allow for facie application of the binder composition to the fibrous substrate in a continuous process and 2) prevent interference with the dispersibility of the binder composition. Therefore, if the triggerable polymer is the anionic ion-sensitive polymer, cobinders which are anionic, nonionic, or very weakly cationic may be preferred. If the triggerable polymer is the cationic ion-sensitive polymer, cobinders which are cationic, nonionic, or very weakly anionic may be added. Additionally, the cobinder desirably does not provide substantial cohesion to the nonwoven material by way of covalent bonds, such that it interferes with the dispersibility of the nonwoven web.

The presence of the cobinder may provide a number of desirable qualities. For example, the cobinder may serve to reduce the shear viscosity of the triggerable polymer, such that the binder composition has improved sprayability over the triggerable binder alone. By use of the term "sprayable" it is meant that these polymers may be applied to the fibrous material or substrate by spraying, allowing the uniform distribution of these polymers across the surface of the substrate and penetration of these polymers into the substrate. The cobinder may also reduce the stiffness of the nonwoven web compared to the stiffness of a nonwoven web to which only the triggerable polymer has been applied.

Reduced stiffness may be achieved if the cobinder has a glass transition temperature, Tg, which is lower than the Tg of the triggerable polymer. In addition, the cobinder may be less expensive than the triggerable polymer and by reducing the amount of triggerable polymer needed, may serve to reduce the cost of the binder composition. Thus, it may be desirable to use the highest amount of cobinder possible in the binder composition such that it does not jeopardize the dispersibility and in-use strength properties of the moist wipe. In one desired aspect of the disclosure, the cobinder replaces a portion of the triggerable polymer in the binder composition so that a desired tensile strength level is achieved. This is done to achieve at least one of the following attributes: lower stiffness, better tactile properties (e.g. lubricity or smoothness) or reduced cost; as compared to a moist wipe having approximately the same tensile strength but containing only the triggerable polymer in the binder composition.

In one aspect of the disclosure, the cobinder, relative to the mass of the binder composition, may be about 10 percent or less, more desirably about 15 percent or less, more desirably 20 percent or less, more desirably 30 percent or less, or more desirably about 45 percent or less. Exemplary ranges of cobinder relative to the solid mass of the binder composition may include from about 1 to about 45 percent, from about 25 to about 35 percent, from about 1 to about 20 percent and from about 5 to about 25 percent.

The cobinder may be selected from a wide variety of polymers, as are known in the art. For example, the cobinder may be selected from poly(ethylene-vinyl acetate), poly (styrene-butadiene), poly(styrene-acrylic), a vinyl acrylic terpolymer, a polyester latex, an acrylic emulsion latex, poly(vinyl chloride), ethylene-vinyl chloride copolymer, a carboxylated vinyl acetate latex, and the like. A variety of additional exemplary cobinder polymers are discussed in U.S. Pat. No. 6,653,406 and U.S. Patent Pub. No. 2003/ 00326963, which are both incorporated herein by reference in their entirety to the extent they are consistent with the present disclosure. Particularly desirable cobinders include—VINNAPAS® EZ123 and VINNAPAS®110, available from Wacker Chemie AG (Wacker Polymers), Munich, Germany.

To prepare the single-ply wipe substrates described herein, the binder composition may be applied to the fibrous material by any known process. Desirably, binder composition application is done by electrostatic spraying. The amount of binder composition is either metered and distributed uniformly onto the fibrous material, or non-uniformly distributed onto the fibrous material.

Once the binder composition is applied to the fibrous material it is dried by any conventional means. Once dry, the single ply wipe substrate may exhibit improved tensile strength when compared to the tensile strength of the untreated, wet-laid or dry-laid fibrous material; and yet should have the ability to rapidly "fall apart" or disperse when placed in tap water.

For ease of application to the fibrous substrate, the binder composition may be dissolved in water, or in a non-aqueous solvent, such as methanol, ethanol, acetone, or the like, with water being the preferred solvent. The amount of binder dissolved in the solvent may vary depending on the polymer used and the fabric application. Desirably, the binder solution contains less than about 18 percent by weight of binder composition solids. More desirably, the binder solution contains less than 16 percent by weight of binder composition solids.

The binder composition may be applied to the fibrous material or substrate to form the nonwoven web using a variety of techniques as described herein.

Wetting Composition

Generally, the wetting composition of the present disclosure contains a carrier medium, silicone oil, an emulsifier system, a stability enhancing system and an insolubilizing agent.

Carrier Medium

Desirably, water serves as a medium for carrying the oil to the skin in an esthetically pleasing manner and at a suitable viscosity as discussed herein. In addition, water aids in the wetting of the wipe substrate. Typically, the wetting compositions of the present disclosure include from about 85% by weight to about 98% by weight water, including from about 90% by weight to about 97% by weight, and including from about 92% by weight to about 96% by weight.

Silicone Oil

The emulsions of the present disclosure include silicone oil sometimes referred to as polymerized dimethylsiloxane. The silicone oil is an active ingredient that functions primarily as a skin protectant against moisture (urine, sweat and overall humidity), and secondarily as an emollient. Desirable oils are those that impart a tactile impression of softness and smoothness, and which do not impart an excessive tactile perception of greasiness, oiliness or coating when incorporated into the wetting composition.

With respect to silicone oils, non-volatile silicone oils may be desirable over volatile silicone oils. Non-volatile silicone oils tend to remain stable when exposed to the environment, tend to provide a lasting tactile impression and tend to form a stable oil layer on the skin.

Mixtures of silicone oils may be used. For example, volatile silicone oils may be combined with non-volatile silicone oils to impart desired esthetic properties, as long as the wetting composition contains sufficient non-volatile silicone to provide a skin barrier layer that is effective for a given application.

In one aspect, the silicone oil is dimethicone (linear polydimethylsiloxane). In this aspect of the disclosure, the emulsions of the present disclosure include from about 1% by weight to about 10% by weight dimethicone, including from about 1% by weight to about 5% by weight, and including from about 1% by weight to about 3% by weight. Other exemplary silicone oils that are suitable for use herein include dimethiconol, ethoxylated dimethicone (linear and pendant varieties), amodimethicone and derivatives thereof, cyclomethicone, alkyl substituted derivatives such as stearyl dimethicone and behenyl dimethicone, phenyl trimethicone and mixtures thereof. Such silicones are commercially available, for example, from the Dow Corning Company of Midland, Mich. under the names XIAMETER PMX-200 Silicone Fluid (Dimethicone), XIAMETER PMX-1184 Silicone Fluid (Trisiloxane and Dimethicone), DOW CORNING 1403 Fluid (Dimethicone and Dimethiconol), DOW CORNING 1501 Fluid (Cyclopentasiloxane and Dimethiconol), DOW CORNING 593 Fluid (Dimethicone and Trimethylsiloxysilicate), DOW CORNING 2502 Fluid (Cetyl Dimethicone), and DOW CORNING 558 Fluid (Phenyl Trimethicone).

Emulsifier System

In addition to the carrier and the barrier composition, the wetting compositions of the present disclosure include an emulsifier system for forming oil-in-water emulsions. The emulsifier system is a synergistic combination of specific ingredients which emulsify other formulation components that would not otherwise mix together in a stable manner. The emulsion breaks upon application to the skin forming a protective oil film. The emulsifier system does not tend to re-emulsify once the emulsion is applied to the skin and exposed to urine or other body fluids. This prevents the oil from being washed away by urine.

Specifically, the emulsifier system includes the following components: either (a) a Gemini surfactant or (b) a phosphate ester.

(a) Gemini Surfactant

Gemini surfactants are a special class of surfactants that contain multiple hydrophobic tails and multiple hydrophilic head groups within the same molecule. Gemini surfactants can be ten to a thousand times more surface active than conventional surfactants with similar but single hydrophilic and hydrophobic groups in the molecule. Gemini surfactants may reduce skin irritation in addition to serving as an emulsifier.

Gemini surfactants are believed to form liquid crystalline lamellar gel networks in the oil phase which result in the formation of very small oil droplets. The small size and gel-like nature of the droplets provides resistance against coalescence of the droplets eventuating in complete oil phase separation. In addition, Gemini surfactants have been shown to not have the HLB dependency for oil emulsification of typical ethoxylated fatty alcohols, ethoxylated fatty esters, and other common non-Gemini surfactant emulsifiers.

While many Gemini surfactants were explored in an effort to create a stable emulsion containing dimethicone and clay, surprisingly, most did not work. One Gemini surfactant that is found to work in an emulsion having 95.15% water is Disodium Ethylene Dicocamide PEG-15 Disulfate. In one aspect of the disclosure this Gemini surfactant is part of a blend. For example, Disodium Ethylene Dicocamide PEG-15 Disulfate may be blended with Behenyl Alcohol (and), Glyceryl Stearate (and) Glyceryl Stearate Citrate, and is available in this form from Sasol North America, Inc. as CERALUTION H.

(b) Phosphate Ester

Emulsifying agents based on phosphate esters are formed by reacting phosphoric acid and a fatty alcohol(s), such as cetearyl alcohol, cetyl alcohol, or behenyl alcohol resulting in an anionic compound. Phosphate esters are well known for their ability to retain active ingredients of interest, such as sunscreens or, in the present invention, ingredients to protect the skin for environmental insults, such as fecal enzymes. As described within the body of the present invention, select anionic phosphate based emulsifiers were compatible with zinc salts, which disperse highly cationic free zinc when dissolved in the emulsion.

Stability Enhancing System

The stability enhancing system is defined by one or more gums and propylene glycol alginate. One desirable gum blend includes xanthan gum and/or guar gum. In certain applications, it may be advantageous to substitute the xanthan gum and/or guar gum with one or more of the following: gellan gum, acacia gum, cellulose gum, dehydroxanthan gum, sclerotium gum and locust bean gum.

Gums are rheological modifiers which are used in conjunction with the propylene glycol alginate. Other classes of rheological modifiers such as starches may be used in combination with propylene glycol alginate provided that a stable emulsion is achieved using less than 0.5% by weight rheological modifiers and the viscosity of the formulation measures below 5,000 centipoise.

Optional Ingredients (a) pH Adjusting Agent

The emulsions of the present disclosure may further include a pH-adjusting agent. Such agents are desirable for the creation of wetting compositions having a pH at or near that of human skin. Therefore, the pH will typically be adjusted as necessary so that the wetting composition of the present disclosure has a pH of from 4 to 7, or more desirably, from 4.5 to 6.5. The pH can be adjusted by adding one or more pH-adjusting agents in an amount effective to provide such pH values ("effective amount"). Agents that may be used to adjust the pH of the wetting compositions include organic and inorganic acids and bases.

For the more desirable wetting compositions of the present disclosure, the wetting composition (in the absence of a pH-adjusting agent) tends to be more basic than desired. Therefore, an acid pH-adjusting agent will typically be used to bring the wetting composition to the desired pH. Acid pH-adjusting agents include organic acids which are relatively non-irritating. Such acids include citric acid, acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid, salicylic acid and mixtures thereof. In one aspect of the present disclosure, a desirable pH-adjusting agent is malic acid.

The amount of the pH-adjusting agent that is employed depends on the equivalent weight of the pH-adjusting agent and the desired pH. Typically, the pH-adjusting agent is used in an amount of from about 0.05% to about 0.5% by weight of the wetting composition. Desirable wetting compositions of the present disclosure include from about 0.1% to about 0.5% percent, and typically about 0.2% to about 0.3% percent of the pH-adjusting agent.

(b) Preservatives

Preservatives function in one or more ways to improve the shelf life of the wetting compositions and products incorporating same. For example, the preservative may be an anti-microbial agent, an anti-bacterial agent, an anti-fungal agent, or a combination thereof.

Anti-microbial agents herein include, but are not limited to, benzethonium chloride, benzisothiazolinone, benzoic acid, benzyl alcohol, 2-Bromo-2-nitropropane-1,3-diol, butylparaben, caprylyl glycol, chlorhexidine digluconate, DMDM hydantoin, diazolidinyl urea, dehydroacetic acid, ethylparaben, iodopropynyl butylcarbamate, methylchloroisothiazolinone, methylisothiazolinone, methyldibromo glutaronitrile, methylparaben, pentylene glycol, phenethyl alcohol, phenoxyethanol, propylparaben, polyaminopropyl biguanide, quaternium-15, salicylic acid, sodium benzoate, sodium methylparaben, sodium dehydroacetate, sodium dehydroacetate, thymol, triclosan and mixtures thereof.

In one aspect of the disclosure, benzoic acid, with or without phenoxyethanol, is effective in preventing the growth of a wide variety of microbes and fungi. Such protection tends to be particularly desirable where the wipe product contains a porous substrate, for example, nonwoven substrates.

The anti-microbial agent is used as may be required in an amount which is effective to provide a suitable shelf life (storage stability, i.e., microorganisms do not grow to a significant extent) (herein alternatively referred to as "an effective amount"). Desirably, moist wipes have a shelf life of at least two years under storage conditions of about 75 degrees Fahrenheit and 50 percent relative humidity. This includes demonstrating sufficient anti-microbial activity as measured in accordance with United States Pharmacopeia test entitled "Microbial Test, Antimicrobial Preservative—Effectiveness". Concentrations necessary to ensure product quality and shelf-life are well understood by those normally skilled in the art.

(c) Chelating Agent

The wetting composition may contain one or more chelating agents. The chelating agent tends to bind metals (e.g., calcium ions, magnesium ions) that may be present in the wetting composition so as to enhance the efficiency of the emulsifier and the anti-microbial agent. Thus, the chelating agent may be considered to provide a level of anti-microbial activity to function as a preservative. The chelating agent may be used in an amount that is effective to bind the aforementioned metals (hereinafter alternatively referred to as an "effective amount"), typically an amount ranging from about 0.01 percent to about 0.20% by weight of the wetting composition. Particularly preferred wetting compositions include from about 0.05% to about 0.20% by weight, more preferably from about 0.05% to about 0.10% by weight. Chelating agents and their use in personal cleansing wetting compositions are well known in the art. Exemplary chelating agents include disodium EDTA, trisodium EDTA, tetrasodium EDTA, and tetrasodium iminodisuccinate.

(d) Other

The wetting composition of the present disclosure may optionally include other ingredients, e.g., fragrance; skin soothing aids such as aloe, lavender, chamomile, green tea, calendula, etc.; skin moisturizers (humectants) such as glycerin, propylene glycol, betaine, and hydroxyethyl urea; or emollients other than those previously described; powders and the like.

Viscosity

While the examples herein show a highly aqueous wetting composition, it is noted that wetting compositions with lower levels of water and thus higher viscosities may be desired, especially of applied to the skin by means other than a moist wipe. For instance, the wetting composition may be formulated to be a lotion, gel or paste. However, for application to wipe substrates as disclosed herein, it is desirable to have a viscosity at 25 degrees Celsius of about 5000 centipoise or less, or in other applications, 4000 centipoise (cps) or less as obtained using a Brookfield DV-II Viscometer with spindle 5 at 6 r.p.m.

Method of Making Moist Wipes

The binder composition may be applied to the fibrous material by means known in the art. Suitable processes for applying the binder composition include, but are not limited to, printing, spraying, electrostatic spraying, the use of metered press rolls and impregnating. The amount of binder composition may be metered and distributed uniformly onto the fibrous material or may be non-uniformly distributed onto the fibrous material.

For ease of application, the binder composition may be applied to the fibrous material in combination with a solvent, a solution or a mixture, with water being the preferred solvent. The amount of binder composition in the solvent may vary, depending on a variety of factors, including the identity and physical characteristics of the binder that is being used, as well as the identity and physical characteristics of the fibrous material to which the binder composition is being applied. Desirably, the mixture or solution of the binder composition may contain up to about 50 weight percent of binder composition solids, such as from about 10 weight percent to 30 weight percent or about 12 weight percent to 25 weight percent binder composition solids.

Once the binder composition is applied to the fibrous material, drying, if necessary, may be achieved by any conventional means known in the art. Once dry, the nonwoven material may exhibit improved tensile strength when compared to the tensile strength of the untreated fibrous material, and yet should have the ability to rapidly "fall apart" or disintegrate when placed in water.

A number of techniques may be employed to manufacture the moist wipes. In one embodiment, these techniques may include the following steps:

1. Providing the fibrous material (e.g., an unbonded airlaid, a tissue web, a carded web, fluff pulp, etc.).
2. Applying the binder composition to the fibrous material, typically in the form of a liquid, suspension, or foam to form the nonwoven web.
3. Drying the nonwoven web.
4. Applying a wetting composition to the nonwoven web to generate the moist wipe.
5. Placing the moist wipe in roll form or in a stack and packaging the product.

Wipes may also be prepared by applying the binder composition to the fibrous material, followed by drying and winding of the resulting nonwoven web into a roll. In this aspect, the wetting composition may be added some time later. For example, large rolls of the dry nonwoven web may be prepared as an intermediate material. This procedure may be advantageous as part of the manufacturing process.

The finished moist wipes may be individually packaged, desirably in a folded condition, in a moisture proof envelope or packaged in containers holding any desired number of sheets in a water-tight package with a wetting composition applied to the wipe. The moist wipes can be stacked in a container in either a folded or unfolded configuration. For example, containers of moist wipes are available wherein each of the moist wipes are arranged in a folded configuration including, but not limited to, c-folded, z-folded, or quarter-folded configurations as are well known to those skilled in the art. Sometimes the folded moist wipes are also interfolded with the moist wipes immediately above and below in the stack of moist wipes. In yet other configurations, the moist wipes can be placed in the container in the form of a continuous nonwoven material. In this case, each individual moist wipe or sheet may be connected, from the first sheet to the last, by similarly weakened lines of perforations or by adhesive bonds. These moist wipes can be stacked on top of each other in a fan folded manner or can be wound into a roll configuration. Some example processes which can be used to manufacture folded moist wipes are described in U.S. Pat. No. 5,540,332 to Kopacz et al. and U.S. Pat. No. 6,905,748 to Sosalla, which are hereby incorporated by reference in a manner that is consistent herewith. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (having a place of business located in San Jose, Calif., U.S.A.); Shimizu Manufacturing (having a place of business located in Japan), and the devices disclosed in U.S. Pat. No. 4,667,890 to Geitman, Jr. which is hereby incorporated by reference in a manner that is consistent herewith. U.S. Pat. No. 6,651,924 Gingras et al. also provides examples of a process for producing coreless rolls of moist wipes, which is hereby incorporated by reference in a manner that is consistent herewith.

Moist Wipe Properties

The moist wipes, as disclosed herein, desirably may be made to have sufficient in-use wet tensile strength, wet thickness, opacity, and dispersibility. They may also be made to be usable without breaking or tearing when in use, to be consumer acceptable, and to provide problem-free disposal once disposed in a household sanitation system.

The moist wipe as disclosed herein desirably may have an in-use wet tensile strength ranging from at least about 100 g/in to about 1000 g/in., such as between about 200 g/in to about 800 g/in., or between about 300 g/in to about 600 g/in. or between about 350 g/in to about 550 g/in.

The moist wipe may be configured to provide all desired physical properties by use of a single or multi-ply moist wipe product, in which two or more plies of nonwoven material are joined together by methods known in the art to form a multi-ply wipe.

The total basis weight of the nonwoven material, consisting of a single or multiple layers of nonwoven material in the final moist wipe product, may be in the range of at least about 25 gsm to about 1.20 gsm, such as between about 40 gsm and 90 gsm, or between about 60 gsm and 80 gsm or between about 70 and 75 gsm.

The wet opacity of the moist wipe, or the tendency of the moist wipe to prevent the transmission of light, may desirably be higher (i.e. less transmitted light) as it provides an indication that the moist wipe will be able to perform its desired function without breaking or tearing. Desirably, the moist wipe, as disclosed herein, may have a wet opacity greater than about 20 percent, such as greater than about 35 percent or greater than about 45 percent.

The average thickness of the moist wipe may be in the range of at least about 0.25 mm to about 1.5 mm, such as between 0.3 mm and 1.0 mm or between 0.5 mm and 1.0 mm.

As mentioned previously, the moist wipes, as disclosed herein, may be sufficiently dispersible so that they lose enough strength to break apart in tap water under conditions typically experienced in household or municipal sanitation systems. Previous methods for measuring dispersibility of the nonwoven materials, whether dry or pre-moistened, have commonly relied on systems in which the material was exposed to shear while in water, such as measuring the time for a material to break up while being agitated by a mechanical mixer. Constant exposure to such relatively high, uncontrolled shear gradients offers an unrealistic and overly optimistic test for products designed to be flushed in a toilet, where the level of shear is extremely weak or brief. Shear rates may be negligible, for example once the material enters a septic tank. Thus, for a realistic appraisal of moist wipe dispersibility, the test methods should simulate the relatively low shear rates the products will experience once they have been flushed in the toilet.

A static soak test, for example, should illustrate the dispersibility of the moist wipe after it is fully wetted with water from the toilet and where it experiences negligible shear, such as in a septic tank. Desirably, the moist wipe may have less than about 100 g/in of tensile strength after 5 h when soaked in water with a total dissolved solids up to 500 ppm and a $CaCO_3$ equivalent hardness up to about 250 ppm. More desirably, the moist wipe may have less than about 100 g/in of tensile strength after 3 h when soaked in water with a total dissolved solids up to 500 ppm and a $CaCO_3$ equivalent hardness up to about 250 ppm. Even more desirably, the moist wipe may have less than about 100 g/in of tensile strength after 1 hour when soaked in water with a total dissolved solids up to 500 ppm and a CaCO₃ equivalent hardness up to about 250 ppm.

Desirably, the moist wipes, as disclosed herein, may possess an in-use wet tensile strength of at least about 150 g/in when wetted with 10 percent to 400 percent of the wetting composition by weight relative to the weight of the nonwoven material, and a tensile strength of less than about 100 g/in when soaked in water with a total dissolved solids up to 500 ppm and a CaCO₃ equivalent hardness up to about 250 ppm after about 24 hours or less, desirably after about one hour.

Most desirably, the moist wipes, as disclosed herein, may possess an in-use wet tensile strength greater than about 300 g/in when wetted with 10 percent to 400 percent of the wetting composition by weight relative to the nonwoven material, and a tensile strength of less than about 100 g/in when soaked in water with a total dissolved solids up to 500 ppm and a CaCO₃ equivalent hardness up to about 250 ppm after about 24 hours or less, desirably after about one hour.

The moist wipe preferably maintains its desired characteristics over the time periods involved in warehousing, transportation, retail display and storage by the consumer. In one embodiment, shelf life may range from two months to two years.

EXAMPLES

The examples demonstrate the use of select phosphate esters or Gemini surfactants in the wetting compositions of the present disclosure. Testing showed that the other ingredients needed to achieve a stable low-viscosity formulation containing 1.5% dimethicone through three freeze-thaw cycles and elevated temperatures were the combination of gum and propylene glycol alginate. Generally, it was determined that the gum(s) and propylene alginate are desirably present in concentrations greater than 0.05% by weight so that the aggregate sum of all three materials did not exceed 0.50% by weight of the finished formulation.

In addition to the emulsifiers provided in Table 1, additional emulsifiers were screened between 1% and 3% by weight alone or in combination with one another with the other ingredients remaining constant in the emulsion. Emulsifiers that failed to produce a stable emulsion include: Glyceryl Stearate, Glyceryl Stearate/PEG-100 Stearate, Sorbitan Sesquioleate, Sorbitan Olivate, Undeceth-3, PEG-20 Methyl Glucose Sesquistearate, Trideceth-3, Trideceth-12, Laureth-9, Behenoyl Stearic Acid, Oleth-2, Oleth-20, Sorbitan Laurate, Sorbitan Palmitate, Sorbitan Oleate, Sorbitan Trioleate, Steareth-2, Steareth-20, Steareth-21, Laureth-23, C11-15 Pareth-15, PPG-24-Buteth-27, High molecular weight polymers of ethylene oxide and propylene oxide, PPG-5-Ceteth-10 Phosphate, Oleth-5 Phosphate, Dioleyl Phosphate, Oleth-3 Phosphate, Oleth-10 Phosphate, Lauryl Phosphate, Trideceth-3 Phosphate, Trideceth-6 Phosphate, Deceth-6 Phosphate, Trilaureth-4 Phosphate, C20-22 Alkyl Phosphate, C20-22 Alcohols, Polyglyceryl-10 Decaoleate, Polyglyceryl-3 Oleate, PEG/PPG-20/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Methoxy PEG/PPG-25/4 Dimethicone, Bis-PEG/PPG-14/14 Dimethicone (and) Dimethicone, PEG-11 Methyl Ether Dimethicone, PEG/PPG-20/22 Butyl Ether Dimethicone, Lauryl PEG-9 Polydimethylsiloxyethyl Dimethicone, PEG-10 Dimethicone, Polyglyceryl-3 Disiloxane Dimethicone, Lauryl Polyglyceryl-3 Polydimethylsiloxyethyl Dimethicone, Lauryl PEG-8 Dimethicone, Sodium Stearate, Sucrose Laurate, Sucrose Myristate, Sucrose Stearate and Methyl Glucose Sesquistearate. Unexpectedly, use of CERALUTION HDisodium Ethylene Dicocamide PEG-15 Disulfate as the only Gemini surfactant in a system containing 94.15% water produced a stable emulsion.

The addition of 2% Sodium Chloride did not negatively impact the stability achieved without the Sodium Chloride.

A 74 gsm dispersible basesheet coated with 235% w/w formulation was used in the following experiments Table 1 shows the composition of the wetting composition of the present disclosure containing a phosphate ester, namely CRODOFOS CS20A.

Examples

TABLE 1 shows the composition of the wetting composition of the present disclosure containing a Phosphate Ester surfactant, namely CRODAFOS CS20A.

TABLE 2 shows the composition of the wetting composition of the present disclosure containing a Gemini surfactant, namely CERALUTION H.

TABLE 3 shows that basesheets coated with wetting compositions containing phosphate ester CRODAFOS CS20A or a Gemini surfactant CERALUTION H lost significant amount of strength following 30 minutes in hard water.

TABLES 4 and 5 show that wetting compositions containing phosphate ester CRODAFOS CS20A and Gemini surfactant CERALUTION H were able to disperse in about 4 or 3 hours, respectively.

TABLE 1

| Trade Name | Vendor | INCI Name | Function | % wt |
|---|---|---|---|---|
| Part A | | | | |
| Water | | Water | Carrier | 92.15 |
| ARAGUM 3173 | TIC Gums | Xanthan Gum (and) Guar Gum (and) Propylene Glycol Alginate | Emulsion Stabilizers | 0.50 |
| PART B | | | | |
| CRODAFOS CS20A | Croda | Cetearyl Alcohol (and) Ceteth-20 Phosphate (and) Dicetyl Phosphate | Emulsifier | 2.00 |
| CETIOL 868 | COGNIS | Ethylhexyl Stearate | Emollient | 1.00 |
| DC 200, 100 CST | Dow Corning | Dimethicone | Skin Protectant | 1.50 |
| PART C | | | | |
| PUROX S | DSM Nutritional Products | Sodium Benzoate | Preservative | 0.45 |
| BRONIDOX 1160 | COGNIS | Phenoxyethanol | Preservative | 0.40 |
| Malic Acid (30% Solution) | Tate & Lyle | Malic Acid | pH Adjuster | 0.00 |
| Part D | | | | |
| Sodium Chloride | Commodity | Sodium Chloride | Binder trigger | 2.00 |

TABLE 2

| Trade Name | Vendor | INCI Name | | % wt |
|---|---|---|---|---|
| Part A | | | | |
| Water | | Water | Carrier | 92.15 |
| ARAGUM 3173 | TIC Gums | Xanthan Gum (and) Guar Gum (and) Propylene Glycol Alginate | Emulsion Stabilizers | 0.50 |
| PART B | | | | |
| CERALUTION H | Sasol | Behenyl Alchol (and) Glyceryl Stearate (and) Glyceryl Stearate Citrate (and) Disodium Ethylene Dicocamide PEG-15 Disulfate | Surfactant | 2.00 |
| CETIOL 868 | COGNIS | Ethylhexyl Stearate | Emollient | 1.00 |
| DC 200, 100 CST | Dow Corning | Dimethicone | Skin Protectant | 1.50 |
| PART C | | | | |
| PUROX S | DSM Nutritional Products | Sodium Benzoate | Preservative | 0.45 |
| BRONIDOX 1160 | COGNIS | Phenoxyethanol | Preservative | 0.40 |
| Malic Acid (30% Solution) | Tate & Lyle | Malic Acid | pH Adjuster | 0.00 |
| Part D | | | | |
| Sodium Chloride | Commodity | Sodium Chloride | Binder Trigger | 2.00 |

TABLE 3

| | Code A | | | Code B | | |
|---|---|---|---|---|---|---|
| Sample ID | In-Use MD Strength (gf/inch) | ½ hr Soak MD Strength (gf/inch) | 1 hr Soak MD Strength (gf/inch) | In-Use MD Strength (gf/inch) | ½ hr Soak MD Strength (gf/inch) | 1 hr Soak MD Strength (gf/inch) |
| 1 | 350.51 | 142.22 | 108.62 | 387.39 | 175.74 | 117.71 |
| 2 | 318.89 | 139.17 | 97.25 | 399.93 | 176.89 | 118.14 |
| 3 | 335.22 | 151.92 | 101.99 | 424.79 | 191.71 | 131.27 |
| 4 | 305.63 | 136.43 | 114.32 | 380.76 | 182.24 | 132.32 |
| 5 | 325.89 | 153.94 | 110.86 | 390.91 | 161.67 | 124.47 |
| 6 | 339.35 | — | — | 393.79 | — | — |
| 7 | 322.47 | — | — | 384.27 | — | — |
| 8 | 306.08 | — | — | 391.04 | — | — |
| 9 | 322.42 | — | — | 401.62 | — | — |
| 10 | 317.69 | — | — | 390.32 | — | — |
| Average | 324.42 | 144.73 | 106.61 | 394.48 | 177.65 | 124.78 |
| St. Dev. | 14.12 | 7.79 | 6.90 | 12.40 | 10.93 | 6.95 |
| % COV | 4.35 | 5.38 | 6.47 | 3.14 | 6.16 | 5.57 |

Code A = CRODOFOS CS20
Code B = CERALUTION H

TABLE 4

| TEST NO. | HOURS | MINUTES | SECONDS |
|---|---|---|---|
| 1 | 4 | 40 | 22 |
| 2 | 4 | 45 | 4 |
| 3 | 4 | 52 | 58 |

TABLE 5

| TEST NO. | HOURS | MINUTES | SECONDS |
|---|---|---|---|
| 1 | 2 | 55 | 10 |
| 2 | 3 | 2 | 39 |
| 3 | 3 | 9 | 40 |

The formulations of Tables 1 and 2 were coated onto base sheets at a 235% add-on level and allowed to equilibrate at room temperature (20-25 degrees Celsius) for 24 hours. From the base sheets, 10 samples for each composition were prepared by adding the appropriate weight of solution to the basesheet and hand rolling the solution until the basesheet was uniformly distributed within the basesheet.

Following the MD Tensile Test method, samples in three sets were tested for wet tensile strength as per the procedure described herein and at the following states: 1) set 1 was tested dry (50% humidity), set 2 was tested after a 30-minute soak in deionized water, and set 3 after a 60-minute soak in deionized water. As shown below, the wetting solution having demonstrated a high wet tensile strength, but lost about 60% of its dry tensile strength following the 30-minute soak.

Experimental Methods

Method of Making Test Wetting Compositions

Generally, the procedure used to make the wetting compositions used for testing includes the following steps:

1. Heat the water phase of the formulation to 75 degrees Celsius while slowly adding the gum blend.
2. Combine materials of the oil phase of the formulation and heat them to 75 degrees Celsius under conditions of constant mixing.
3. Add the oil phase to the water phase and homogenize the mixture at 5000 to 7000 rpm for five minutes using a SILVERSON homogenizer available from Silverson Machines, Inc.
4. Cool the mixture to 35 degrees Celsius under conditions of constant mixing.
5. Add preservatives if desired.
6. Adjust pH to 4.5+/−0.5 using an acid.
7. Homogenize the mixture again for two minutes at 2000 to 3000 rpm.

MD Tensile Test

The "MD tensile strength" is the peak load in grams-force per inch of sample width when a test sample is pulled to rupture in the machine direction.

Test samples were prepared and conditioned, and tensile tests were performed at the ambient conditions of 23+/−2 degrees centigrade and 50+/−5 percent relative humidity. To prepare test samples, moist wipes were cut into 1-inch wide strips (cut from the center of the wipes) in the machine direction (MD) using a JDC Precision Sample Cutter (Thwing-Albert Instrument Company, Philadelphia, Pa., Model No. JDC 3-10, Serial No. 37333).

For purposes herein, tensile strength may be measured using a pneumatically controlled Constant Rate of Elongation (CRE) tensile tester having minimum of a 1-inch jaw width (sample width) and a jaw span of 3+/−0.04 inches (gauge length). The actual instrument used for measuring tensile strength was a MTS SINERGY 200 tensile tester, available from MTS Systems Corp., Eden Prairie, Minn. The MTS load cell had a maximum capacity of 50 Newtons. The data acquisition software was MTS TESTWORKS® for Windows, Ver. 4.0, also commercially available from MTS Systems Corp. The top and bottom jaws provided a maximum pressure of 60 P.S.I., the break sensitivity was set at 40 percent, and the data acquisition rate was 100 data points per second.

To begin the test, a single sample is placed in the jaws of the instrument, centered both vertically and horizontally. Tensile force is applied by separating the jaws at a rate of 25.4 centimeters per minute. Sample failure was deemed to occur when the force dropped to 40 percent of the peak load. The peak load expressed in grams-force was recorded as the tensile strength of the specimen. At least twelve representative samples were tested for each product code.

Slosh Box Test

To perform the slosh box test one uses a bench-scaled apparatus to evaluate how flushable consumer products breakup or disperse as they travel through a wastewater collection system. In this test method, a clear plastic tank was loaded with a single moist wipe and tap water or raw wastewater. The container was oscillated in an up-and-down fashion by a cam system operated at a specified rotational speed. The initial breakup point and the time for dispersion of the moist wipe into pieces measuring 1 in×1 in (25 mm×25 mm) was recorded. This dimension was used because it reduces the potential of product recognition. The testing time may be extended until the moist wipe is fully dispersed into clumps of fibers. After dispersal, the resulting pieces of the moist wipe were screened and weighed to determine the rate and level of disintegration.

Test Parameters:

The slosh-box water transport simulator consists of a transparent plastic tank that is mounted on an oscillating platform having speed and holding time controls. The oscillating platform has an angle of incline produced by the cam system and can mimic the normal back-and forth movement of wastewater as it flows through sewer pipe. The water motion produced is equivalent to 60 cm/s (2 ft/s), which is the minimum design standard for wastewater flow rate in an enclosed collection system. The rate of oscillation is controlled mechanically by the rotation of the cam system and should be measured periodically throughout the test.

Test Initiation:

2000 mL of room temperature tap water (softened and/or non-softened) or raw wastewater was placed in the plastic tank. The timer was set for a 6 hour agitation period and the cycle speed was set for 26 rpm. The pre-weighed product was placed in the tank and observed during the agitation period. Only single moist wipes were evaluated at one time. A minimum of one gram of test product was used so that adequate loss measurements could be made. The time to break up into two sections was recorded.

Freeze-Thaw Stability Test

The purpose of this test is to demonstrate formulation stability upon exposure to possible freezing during shipping or storage. The test is performed by freezing the composition at 20 degrees Celsius. Once frozen, the composition is allowed to completely thaw at room temperature. This freeze-thaw cycle is conducted for a total of three times. The test results are determined by visual inspection for phase separation.

Basis Weight Test

The dry basis weight of the basesheet material forming the wet wipes in the stack can be obtained using the ASTM active standard D646-96(2001), Standard Test Method for Grammage of Paper and Paperboard (Mass per Unit Area), or an equivalent method.

Sheet-Sheet Adhesion Test

A 180 degree t-peel measurement was used to determine the sheet-to-sheet adhesion between adjacent wet wipe surfaces. The method for the 180 degree t-peel measurement was based upon ASTM D1876-01 Standard Test Method for Peel Resistance of Adhesives (T-Peel Test) with the following modifications. A crosshead speed of 20 inches/minute with a gauge length of 1.5 inches was used for all measurements. Measurements were recorded between 0.5 inches and 6.0 inches, with the end test point at 6.5 inches. Wet wipes were aged prior to measurement according as described in the examples. The aged wipes were cut into samples 1 inch wide with a depth of at least two layers thick.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations without departing from the scope of the disclosure, it is intended that all matter contained in the above description shall be interpreted as illustrative and not in a limiting sense.

The invention claimed is:

1. A moist wipe comprising:
   a stable wetting composition for the prevention of skin irritation, the stable wetting composition comprising:
   disodium ethylene dicocamide PEG-15 disulfate;
   a gum blend comprising a gum and propylene glycol alginate, wherein the amount of the gum blend is 0.01% to 0.5% by weight; wherein the gum is selected from the group consisting of guar gum, gellan gum, acacia gum, cellulose gum, dehydroxanthan gum, sclerotium gum, locust bean gum and combinations thereof;
   1% to 10% by weight silicone oil;
   85% to 98% by weight water;
   a salt containing monovalent and/or divalent ions; and
   a dispersible substrate onto which the stable wetting composition has been applied; wherein the amount of salt is that which is effective to preserve the wet strength of the dispersible substrate during storage; wherein the viscosity of the stable wetting composition is less than 5000 centipoise; and wherein the stable wetting composition maintains stability after at least one freeze-thaw cycle.

2. The moist wipe of claim 1 wherein the silicone oil consists of dimethicone.

3. The moist wipe of claim 1 wherein the silicone oil is selected from the group consisting of dimethicone, amodimethicone and derivatives thereof, dimethiconol, cyclomethicone, stearyl dimethicone, behenyl dimethicone, phenyl trimethicone and combinations thereof.

4. The moist wipe of claim 1 further comprising a preservative.

5. The moist wipe of claim 1 further comprising a pH adjusting agent.

6. The moist wipe of claim 1 wherein the gum consists of xanthan gum and guar gum.

7. The moist wipe of claim 1 wherein the substrate comprises spunbond fabric, meltblown fabric, knit fabric, wet-laid fabric, scrims or needle-punched webs.

8. The moist wipe of claim 1 wherein the substrate is airlaid nonwoven fabric.

9. A moist wipe comprising:
a stable wetting composition for the prevention of skin irritation, the stable wetting composition having a viscosity of less than 5000 centipoise and comprising:
disodium ethylene dicocamide PEG-15 disulfate;
xanthan gum, guar gum and propylene glycol alginate;
1% to 10% by weight dimethicone;
85% to 98% by weight water; and
a salt containing monovalent and/or divalent ions; and
a non-woven substrate onto which the stable wetting composition has been applied; wherein the stable wetting composition maintains stability after at least one freeze-thaw cycle.

10. A stable wetting composition for a moist wipe comprising:
disodium ethylene dicocamide PEG-15 disulfate;
a gum blend comprising xanthan gum, guar gum and propylene glycol alginate, wherein the amount of gum blend is 0.05% to 0.5% by weight;
1% to 10% by weight silicone oil;
1% to 3% salt containing monovalent and/or divalent ions; and
95% to 98% by weight water;
wherein the viscosity of the stable wetting composition is less than 5000 centipoise; and
wherein the stable wetting composition maintains stability after at least one freeze-thaw cycle.

11. The moist wipe of claim 1, wherein the stable wetting composition maintains stability after at least three freeze-thaw cycles.

12. The moist wipe of claim 9, wherein the stable wetting composition maintains stability after at least three freeze-thaw cycles.

13. The stable wetting composition for a moist wipe of claim 10, wherein the stable wetting composition maintains stability after at least three freeze-thaw cycles.

* * * * *